United States Patent [19]
Simonnet et al.

[11] Patent Number: 5,919,487
[45] Date of Patent: Jul. 6, 1999

[54] NANOPARTICLES COATED WITH A LAMELLAR PHASE BASED ON SILICONE SURFACTANT AND COMPOSITIONS CONTAINING THEM

[75] Inventors: Jean-Thierry Simonnet; Pascal Richart, both of Paris, France

[73] Assignee: L'Oreal, Paris, France

[21] Appl. No.: 08/771,837

[22] Filed: Dec. 23, 1996

[30] Foreign Application Priority Data

Dec. 21, 1995 [FR] France .................................... 95 15293

[51] Int. Cl.⁶ .............................. A61K 9/16; A61K 9/50
[52] U.S. Cl. .............................. 424/490; 424/489; 424/47
[58] Field of Search .............................. 424/450, 47, 489, 424/490

[56] References Cited

U.S. PATENT DOCUMENTS

| 5,169,622 | 12/1992 | Kopolow et al. | 424/47 |
| 5,364,633 | 11/1994 | Hill et al. | 424/450 |
| 5,411,744 | 5/1995 | Hill et al. | 424/450 |

FOREIGN PATENT DOCUMENTS

| 0 447 318 | 9/1991 | European Pat. Off. |
| 0 511 092 | 10/1992 | European Pat. Off. |
| 0 641 557 | 3/1995 | European Pat. Off. |

OTHER PUBLICATIONS

Anal. Chem, (1993), vol. 65, pp. 1779–1784, "Enzyme Immunoassay Using a Rat Prolactin–Alkaline Phosphatase Recombinant Tracer", *Daniel Gillet, et al.*

*Primary Examiner*—Thurman K. Page
*Assistant Examiner*—William E. Benston, Jr.
*Attorney, Agent, or Firm*—Oblon, Spivak, McClelland, Maier & Neustadt, P.C.

[57] ABSTRACT

The present invention relates to nanoparticles, and in particular nanocapsules, provided with a lamellar coating obtained from a silicone surfactant, and to their use in a composition, in particular a topical composition, for treatment of the skin, mucosae, nails, scalp and/or hair.

21 Claims, No Drawings

NANOPARTICLES COATED WITH A LAMELLAR PHASE BASED ON SILICONE SURFACTANT AND COMPOSITIONS CONTAINING THEM

BACKGROUND OF THE INVENTION

1. Field of the Invention

The present invention relates to nanoparticles provided with a lamellar coating consisting of a silicone surfactant, and to their use in a composition, in particular in a topical composition for treatment of the skin, mucosae, nails, scalp and/or hair.

2. Description of the Background

It is known in the cosmetic and dermatological fields, for example from EP-A-557489, EP-A-447318 and WO-A-93/25195, to apply to the skin active agents trapped in spherules in order to improve the efficacy of these active agents. These spherules are, in particular, nanoparticles of polymer, the small size of which, of the order of 10 to 1000 nm, permits better penetration into the upper layers of the epidermis. The term nanoparticles encompasses on the one hand nanospheres and on the other hand nanocapsules. "Nanospheres" denotes nanoparticles consisting of a porous polymer matrix on which the active agent is absorbed and/or adsorbed, and "nanocapsules" denotes nanoparticles consisting of a polymer membrane which encapsulates an oily core.

When nanoparticles are incorporated in compositions, a release of the active agents into the composition frequently takes place. In the particular case of nanocapsules, when they are incorporated in a composition containing an oily phase, such as for example emulsions, the active agents encapsulated in the oily core migrate to the oily phase of the composition. This premature release of the active agents into the composition makes their encapsulation in nanoparticles ineffective.

To remedy this drawback, it is known to coat the nanoparticles with a lamellar phase. Hitherto, in order to obtain a coating having sufficient freedom from leakage, a lecithin-based lamellar coating was used, as described in EP-A-447318. In point of fact, lecithin possesses the drawback of being sensitive to oxidation, which results in a yellowing of the nanoparticles, imparting to the composition containing them an appearance which is rather distasteful to the user.

The need hence remains for nanoparticles provided with a lamellar coating having good freedom from leakage and not possessing the drawbacks mentioned above.

Applicants have found, unexpectedly, a lamellar coating enabling this objective to be achieved.

SUMMARY OF THE INVENTION

In effect, Applicants found that the use of a silicone surfactant enabled nanoparticles to be obtained that were less sensitive to oxidation and hence whiter. In addition, by means of the use of a silicone surfactant, the manufacture of the coated nanoparticles is carried out with an appreciable gain in time. In effect, the presence of the silicone surfactant decreases foam formation during their manufacture.

DETAILED DESCRIPTION OF THE INVENTION

Thus, the subject of the present invention is a nanoparticle ranging in size from 10 to 1000 nm, composed of a polymer encapsulating an oily phase and coated with a lamellar coating, characterized in that the lamellar coating consists of at least one silicone surfactant containing at least a oxyethylenated and/or oxypropylenated chain.

The nanoparticles according to the invention preferably range in size from 10 to 600 nm.

A silicone surfactant is a silicone compound containing at least a oxyethylenated —$OCH_2CH_2$— and/or oxypropylenated —$OCH_2CH_2CH_2$— chain. Silicone surfactants which may be used according to the present invention include those described in U.S. Pat. No. 5,364,633 and U.S. Pat. No. 5,411,744. These references describe the use of silicone surfactants for preparing lipid vesicles. However, they do not disclose or suggest the possibility of forming lamellar phases around nanoparticles from such surfactants.

Preferably, the silicone surfactant used according to the present invention is a compound of formula (I):

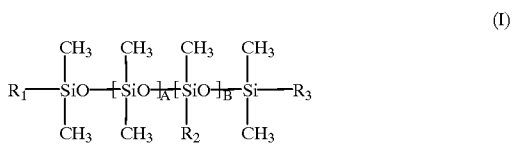

(I)

in which $R_1$, $R_2$ and $R_3$, independently of one another, represent a $C_1$–$C_6$-alkyl radical or a radical $(CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being a hydrogen, an alkyl radical or an acyl radical;

A is an integer ranging from 0 to 200;

B is an integer ranging from 0 to 50; on condition that A and B are not equal to zero at the same time; x is an integer ranging from 1 to 6; y is an integer ranging from 1 to 30; z is an integer ranging from 0 to 5.

According to a preferred embodiment of the invention, in the compound of formula (I), the alkyl radical is a methyl radical, x is an integer ranging from 2 to 6 and y is an integer ranging from 4 to 30.

An example of silicone surfactants of formula (I) are the compounds of formula (II):

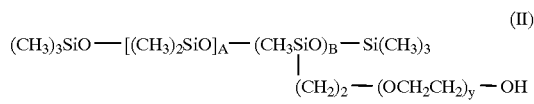

(II)

in which A is an integer ranging from 20 to 105, B is an integer ranging from 2 to 10 and y is an integer ranging from 10 to 20.

Compounds of formula (III):

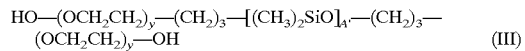

(III)

in which A' and y are integers ranging from 10 to 20, may also be used as an example of silicone surfactants of formula (I).

It is possible to use as compounds of the invention those sold by the company Dow Corning under the names DC 5329, DC 7439-146, DC 2-5695 and Q4-3667.

The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

The polymers constituting the nanoparticles according to the invention may be biodegradable or non-biodegradable polymers. The nanoparticles made of biodegradable polymers penetrate the skin and degrade in the epidermis under the action of the enzymes which are present therein, while the nanoparticles made of non-biodegradable polymers penetrate only into the superficial layers of the stratum corneum and are eliminated naturally during renewal of the skin.

As biodegradable polymers, any polymer capable of being degraded by the enzymes of the skin may be used, and in particular those polymers disclosed in EP-A-447318. Poly-L- and -DL-lactides and polycaprolactones are especially preferred as biodegradable polymers.

The non-biodegradable polymers which can be used according to the invention may be chosen from all polymers which are not degraded by the enzymes of the skin, and in particular those polymers disclosed in EP-A-557489. Among non-biodegradable polymers, copolymers of vinyl chloride and vinyl acetate and copolymers of methacrylic acid and methacrylic acid methyl ester are especially preferred.

Preferably the nanoparticles of the invention are nanocapsules. To this end, the polymers described above are especially suitable for obtaining these nanocapsules.

In the nanoparticles of the invention, the weight ratio of the silicone surfactant to the polymer advantageously ranges from 0.1 to 2, and preferably from 0.5 to 1.

The nanoparticles generally contain at least one trapped active agent, constituting on its own the oily phase or contained in a carrier constituting the oily phase.

The weight ratio of the polymer to the active agent and/or the carrier advantageously ranges from 0.01 to 1, and preferably from 0.05 to 0.5.

The nanoparticles according to the invention are prepared according to the usual methods, and in particular according to the methods described in EP-A-447318 and WO-A-93/25195.

According to some of these methods, a surfactant is used during the manufacture of the nanoparticles. Surfactants which can be used in these methods include, for example, condensates of ethylene oxide and propylene oxide, and in particular poloxamers such as the one sold under the name "Pluronic F-68" by the company BASF.

The coated nanoparticles according to the invention are used, in particular, in compositions for topical application, especially cosmetic and/or dermatological compositions.

The subject of the present invention is also a composition, more especially for topical application, characterized in that it contains nanoparticles as defined above in a suitable medium.

The nanoparticles are generally introduced in the form of a suspension into the composition.

"Suitable medium" is understood to mean the medium used for the manufacture of the nanoparticles and/or a topically acceptable medium, that is to say a medium compatible with the skin, mucosae, nails, scalp and hair.

Preferably, the nanoparticles represent from 0.1 to 40% by weight, and more preferably from 5 to 25% by weight, relative to the total weight of the composition.

In the composition according to the invention, the active agent possibly trapped can be any active agent capable of having cosmetic and/or therapeutic activity. This active agent may be oleophilic or hydrophilic. It may be chosen, inter alia, from emollients, humectants, free-radical scavengers, antioxidant agents, anti-inflammatory agents, vitamins, depigmenting agents, anti-acne agents, antiseborrhoeic agents, keratolytic agents, slimming agents, skin coloring agents, sun screen agents, essential oils, pigments, tan-accelerating agents, perfumes, colorants, melanoregulatory agents, anti-wrinkle and anti-ageing agents, liporegulatory agents, antibacterial agents, antifungal agents, antiperspirants, deodorants, immunomodulatory agents, cicatrizing agents, vascular protective agents, skin conditioning agents and mixtures thereof.

In the nanocapsules, the active agent is preferably an oleophilic active agent, alone or in solution in an oily carrier, but it can also be in the form of a dispersion, suspension or emulsion. The oily carrier is preferably chosen from simple or modified triglycerides, silicone oils, in particular volatile silicone oils, and non-silicone oils, in particular mineral oils. Caprylic/capric acid triglycerides may be used, for example, as an oily carrier.

Trapped active agents which can be used, in particular, in the nanocapsules according to the invention, include, in particular, the active agents customarily used in the fields in question, and, for example, vitamins such as tocopherol (vitamin E) and its derivatives, for instance tocopherol acetate, retinol (vitamin A) and its derivatives such as retinol palmitate, essential fatty acids and more especially vitamin F; keratolytic agents such as salicylic acid and its derivatives, for instance, in particular, the ones described in FR-A-2581542, EP-A-378936 and EP-A-570230, especially 5-n-octanoylsalicylic, 5-n-decanoylsalicylic, 5-n-dodecanoylsalicylic, 5-n-octylsalicylic, 5-n-heptyloxysalicylic and 4-n-heptyloxysalicylic acids.

The composition according to the invention may take any form suitable for topical application, and in particular the form of a solution, water-in-oil or oil-in-water emulsion or aqueous dispersion based on ionic and/or nonionic lipid vesicles, generally known as liposomes. It may constitute, for example, a serum, a milk or a cream.

The composition according to the invention may also take the form of an oil-in-water emulsion, the droplets of oil dispersed in water being provided with a lamellar coating, as described in EP-A-641557.

The amounts of the different constituents of the compositions according to the invention are those traditionally used in the field in question.

When the composition of the invention is an emulsion, the proportion of the fatty phase may range from 5 to 80% by weight, and preferably from 5 to 50% by weight, relative to the total weight of the composition. The oils, emulsifiers and coemulsifiers used in the composition in emulsion form are chosen from those traditionally used in the fields in question. The emulsifier and coemulsifier are present in the composition in a proportion ranging from 0.3 to 30% by weight, and preferably from 0.5 to 20% by weight, relative to the total weight of the composition. The emulsion can, in addition, contain lipid vesicles.

In a known manner the composition of the invention can also contain adjuvants which are customary in the cosmetic and/or dermatological fields, such as gelling agents, active agents, preservatives, antioxidants, complexing agents, solvents, perfumes, fillers, sunscreen agents, bactericides, odor absorbers and colouring matter. The amounts of these different adjuvants are those traditionally used in the field in question, and are, for example, from 0.01 to 20% of the total weight of the composition. These adjuvants, depending on their nature, may be introduced into the fatty phase, into the aqueous phase and/or into the lipid vesicles. Oils which can be used in the invention include, with examples in parentheses, mineral oils (liquid paraffin), vegetable oils (avocado oil, sweet almond oil), animal oils, synthetic oils (stearyl heptanoate, capric-caprylic acid triglycerides), silicone oils (volatile silicone oil, polydimethylsiloxane) and fluorinated oils. Fatty alcohols (acetyl alcohol), fatty acids (stearic acid) and waxes may also be used as fatty substances.

Emulsifiers which can be used in the invention include, for example, glycerol monostearate, oxyethylenated sorbitan monostearate, sucrose distearate and cetearyl alcohol polyethylene glycol ether.

Hydrophilic gelling agents include carboxyvinyl polymers (carbomer), acrylic copolymers, polyacrylamides, polysaccharides, natural gums and clays, and lipophilic gelling agents include modified clays such as bentones, metal salts of fatty acids, ethylcellulose or alternatively polyethylene.

As hydrophilic active agents, polyols (glycerol), amino acids (hydroxyproline), water-soluble vitamins (D-panthenol) and polysaccharides (sodium hyaluronate) may be used.

As lipophilic active agents, retinol (vitamin A) and its derivatives (retinol palmitate) and tocopherol (vitamin E) and its derivatives may be used.

The composition according to the invention may be used, in particular, for treatment of the skin, mucosae, nails, scalp and/or hair, especially for the treatment of skin ageing (wrinkles, radiance of the complexion). Thus, the subject of the invention is also the use of the composition defined above for the cosmetic and/or dermatological treatment of the skin against ageing.

Its subject is also a method of therapeutic and/or non-therapeutic treatment of the skin and/or mucosae and/or nails and/or scalp and/or hair, characterized in that it consists in applying the composition as defined above to the skin and/or mucosae and/or nails and/or scalp and/or hair.

The examples below of compositions according to the invention are given by way of illustration and without implied limitation. The amounts therein are given in % by weight.

EXAMPLE 1

Preparation of Coated Nanocapsules According to the Invention, Containing 5% of Tocopherol Acetate In a 500-ml beaker, 1 g of polycaprolactone, 5 g of tocopherol acetate and 1 g of DC 2-5695 are dissolved in 200 ml of acetone with gentle stirring. In another beaker, 0.5 g of Pluronic F-68 is dissolved in 200 g of distilled water with stirring. The acetone phase is then poured into the aqueous phase while stirring is maintained. The acetone and a portion of the water are then evaporated off with a rotary evaporator until 100 ml of solution are obtained. A suspension of nanocapsules having an average diameter of 300 nm is obtained.

EXAMPLE 2

Preparation of Coated Nanocapsules According to the Invention, Containing 2.5% of Retinol Palmitate The procedure is as in Example 1, replacing tocopherol acetate with 5 g of a mixture composed of equal proportions of retinol palmitate and caprylic/capric acid triglycerides.

REFERENCE EXAMPLE

Preparation of Coated Nanocapsules According to the Prior Art, Containing 5% of Tocopherol Acetate The procedure is as in Example 1, using 5 g of tocopherol acetate and replacing DC 2-5695 with 1 g of lecithin.

The nanocapsules obtained according to Example 1 and those obtained according to the reference example were compared. The results are presented in the following table:

| Results | Example 1 (according to the invention) | Reference example |
|---|---|---|
| Manufacturing time | 4 hours | 5 hours |
| Color of the nanocapsules | White | Ivory |
| Microscopic appearance | fine | fine |
| % of oil extracted in oily medium relative to the initial amount of oil | | |
| into perhydrosqualene | 5% | 2% |
| into a volatile silicone | 4% | 4% |
| into octyldodecanol | 4% | 3% |
| On application to the skin | Gentle | Harsh |

These results show that the coating obtained with the silicone surfactants according to the invention displays a freedom from leakage which is as good as the coating of the prior art while at the same time not oxidizing. Moreover, the preparation of the nanocapsules coated with the surfactants according to the invention is faster than that of the nanocapsules of the prior art.

EXAMPLE 3

Skincare Cream

| | |
|---|---|
| Nanocapsules obtained according to Example 1 | 10% |
| Fatty phase: | |
| Ceteareth-33 (cetearyl alcohol polyethylene glycol ether | 0.4% |
| Glycerol monostearate | 0.8% |
| Polydimethylsiloxane | 0.6% |
| Capric/caprylic acid triglycerides | 10% |
| Liquid paraffin | 6% |
| Cetyl alcohol | 0.6% |
| Aqueous phase: | |
| Preservative | 0.3% |
| Demineralized water | qs 100% |

The procedure for preparing this cream was as follows: the fatty phase and the aqueous phase were brought separately to 80° C., the fatty phase was then introduced into the aqueous phase with brisk stirring and this stirring was maintained until the temperature of the mixture reached 50° C. The mixture was then stirred more slowly until the temperature of the mixture reached 30° C. The suspension of nanocapsules according to Example 1 was then introduced with gentle stirring.

A white cream was obtained, capable of improving, by daily application, the radiance of the complexion of the facial skin.

EXAMPLE 4

Day Cream for the Face

| | |
|---|---|
| Phase A: | |
| Sucrose distearate | 1.75% |
| Oxyethylenated sorbitan stearate (Tween 61 sold by the company ICI) | 1.15% |
| Stearic acid | 0.75% |
| Stearyl heptanoate | 4% |
| Liquid paraffin | 1.5% |
| Avocado oil | 3% |

| | |
|---|---|
| Sweet almond oil | 3% |
| Volatile silicone oil | 2.5% |
| Retinol palmitate, 1500 IU/mg | 0.5% |
| Preservatives | 0.2% |
| Phase B: | |
| Glycerol | 5% |
| Triethanolamine | 0.35% |
| Demineralized water | 58.3% |
| Phase C: | 10% |
| Suspension of nanocapsules according to Example 1 | |
| Phase D: | |
| Carbomer | 0.3% |
| Demineralized water | 7.7% |

The cream obtained containing coated nanocapsules also comprises droplets of oil provided with a lamellar coating according to EP-A-641557.

The procedure for preparing this cream was as follows: the constituents of phase A were mixed and the mixture was heated to 60° C.; phase B was treated likewise; phase B was then introduced into phase A with stirring; the mixture obtained was thereafter homogenized three times in succession in a high pressure homogenizer at 500 bars ($5 \times 10^7$ Pa). The mixture was then brought down to room temperature and phase C was introduced into it with light stirring. Phase D was thereafter introduced with care and the constituents were mixed gently until distributed homogeneously.

A shiny, smooth white cream having a very fine texture was obtained, which could be applied daily and was capable of treating wrinkles and of improving the complexion.

EXAMPLE 5

Anti-Ageing Serum (Composition with Liposomes)

| | |
|---|---|
| Phase A: | |
| Sorbitan palmitate (Span 40 sold by the company ICI) | 0.475% |
| Cholesterol | 0.475% |
| N-Stearoylglutamic acid monosodium salt (Acylglutamate HS11 sold by the company Ajinomoto) | 0.05% |
| Phase B: | |
| Demineralized water | 15% |
| Glycerol | 3% |
| Hydroxyproline | 1% |
| Phase C: | |
| Demineralized water | 52.9% |
| Preservatives | 0.3% |
| D-Panthenol | 1.5% |
| Sodium hyaluronate | 0.1% |
| Phase D: | 15% |
| Suspension of nanocapsules of Example 2 | |
| Phase E: | |
| Carbomer | 0.2% |
| Triethanolamine | 0.2% |
| Demineralized water | 9.8% |

The procedure for preparing this cream was as follows: Phase A was introduced into phase B, heated beforehand to 80° C., with stirring over 1 hour. The mixture was then homogenized three times in succession with a high pressure homogenizer at 600 bars ($6 \times 10^7$ Pa). The mixture was thereafter brought down to room temperature and phase C was introduced into it with light stirring. Phase D was thereafter introduced with care and the constituents were mixed gently until distributed homogeneously. Lastly, phase E was introduced gradually and stirring was maintained until the mixture was completely homogeneous.

A serum imparting a very fresh sensation on application was obtained.

The disclosure of France priority patent Application 95-15293 filed Dec. 21, 1995 is hereby incorporated by references.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. Nanoparticle ranging in size from 10 to 1000 nm composed of a polymer encapsulating an oily phase and coated with a lamellar coating, wherein the lamellar coating comprises at least one silicone surfactant containing at least a oxyethylenated and/or oxypropylenated chain, wherein the silicone surfactant is a silicone compound of formula (I):

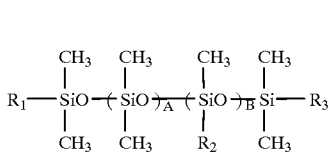

in which:

R$_1$, R$_2$ and R$_3$, independently of one another, represent a C$_1$–C$_6$-alkyl radical or a radical (CH$_2$)$_x$—(OCH$_2$CH$_2$)$_y$—(OCH$_2$CH$_2$CH$_2$)$_z$—OR$_4$, at least one radical R$_1$, R$_2$ or R$_3$ not being an alkyl radical; R$_4$ being a hydrogen, an alkyl radical or an acyl radical;

A is an integer ranging from 0 to 200;

B is an integer ranging from 0 to 50; provided that A and B are not equal to zero at the same time;

x is an integer ranging from 1 to 6;

y is an integer ranging from 1 to 30; and z is an integer ranging from 0 to 5.

2. Nanoparticle according to claim 1, wherein the silicone surfactant is a compound of formula (I) in which the alkyl radical is a methyl radical, x is an integer ranging from 2 to 6 and y is an integer ranging from 4 to 30.

3. Nanoparticle according to claim 1, wherein the silicone surfactant is a compound of formula (II):

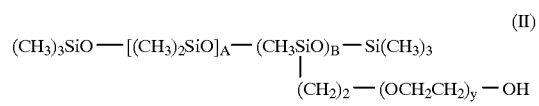

in which A is an integer ranging from 20 to 105, B is an integer ranging from 2 to 10 and y is an integer ranging from 10 to 20.

4. Nanoparticle according to claim 3, wherein the silicone surfactant is selected from the compounds of formula (II) in which A is 22, B is 2 and y is 12; A is 103, B is 10 and y is 12; and A is 27, B is 3 and y is 12.

5. Nanoparticle according to claim 1, wherein the silicone surfactant is a compound of formula (III):

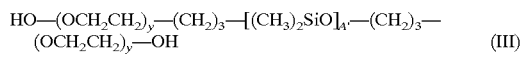

in which A' and y are integers ranging from 10 to 20.

6. Nanoparticle according to claim 5, wherein the silicone surfactant is a compound of formula (III) in which A is 15 and y is 13.

7. Nanoparticle according to claim 1, wherein the nanoparticle ranges in size from 10 to 600 nm.

8. Nanoparticle according to claim 1, wherein the polymer is selected from the group comprising poly-L- and -DL-lactides, polycaprolactones, copolymers of vinyl chloride- and vinyl acetate and copolymers of methacrylic acid and methacrylic acid methyl ester.

9. Nanoparticle according to claim 1, wherein the polymer is a biodegradable polymer.

10. Nanoparticle according to claim 1, wherein the nanoparticle is a nanocapsule.

11. Nanoparticle according to claim 1, wherein the weight ratio of the silicone surfactant to the polymer ranges from 0.1 to 2.

12. Nanoparticle according to claim 1, wherein the nanoparticle contains at least one active agent.

13. Nanoparticle according to claim 12, wherein the weight ratio of the polymer to the active agent ranges from 0.01 to 1.

14. Nanoparticle according to claim 12, wherein the active agent is an oleophilic active agent.

15. Nanoparticle according to claim 12, wherein the active agent is selected from the group consisting of retinol and its derivatives and tocopherol and its derivatives.

16. Composition containing nanoparticles according to claim 1 in a suitable medium.

17. Composition according to claim 16, wherein the nanoparticles represent from 0.1 to 40% by weight of the total weight of the composition.

18. Composition according to claim 16, wherein the composition is in the form of an emulsion or of a dispersion of lipid vesicles.

19. Composition according to claim 16, containing at least one cosmetic and/or dermatological agent.

20. A method for the cosmetic and/or dermatological treatment of the skin against ageing comprising applying the composition of claim 19 to the skin.

21. A method of non-therapeutic treatment of at least one substrate selected from the group consisting of the skin, mucosae, nails, scalp and hair, which comprises applying the composition according to claim 19 to said substrate.

* * * * *